United States Patent
Hladio et al.

(10) Patent No.: US 11,007,013 B2
(45) Date of Patent: May 18, 2021

(54) SYSTEM, METHOD AND APPARATUS FOR AUTOMATIC REGISTRATION IN COMPUTER ASSISTED BONE MILLING SURGERY

(71) Applicant: INTELLIJOINT SURGICAL INC., Waterloo (CA)

(72) Inventors: Andre Novomir Hladio, Waterloo (CA); Joseph Arthur Schipper, Kitchener (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 203 days.

(21) Appl. No.: 16/401,177

(22) Filed: May 2, 2019

(65) Prior Publication Data
US 2019/0336220 A1   Nov. 7, 2019

Related U.S. Application Data

(60) Provisional application No. 62/665,730, filed on May 2, 2018.

(51) Int. Cl.
*A61B 34/10* (2016.01)
*A61B 34/30* (2016.01)
*A61B 17/16* (2006.01)
*A61F 2/32* (2006.01)

(52) U.S. Cl.
CPC ............. *A61B 34/10* (2016.02); *A61B 34/30* (2016.02); *A61B 17/1664* (2013.01); *A61B 2017/1602* (2013.01); *A61B 2034/102* (2016.02); *A61B 2034/108* (2016.02); *A61F 2/32* (2013.01)

(58) Field of Classification Search
CPC ............................... A61B 34/10; A61B 34/30
See application file for complete search history.

(56) References Cited

U.S. PATENT DOCUMENTS

| | | | | |
|---|---|---|---|---|
| 8,052,695 | B2 * | 11/2011 | Kienzle, III | A61B 17/1703 606/130 |
| 8,114,086 | B2 * | 2/2012 | Claypool | A61B 17/155 606/87 |
| 8,118,815 | B2 * | 2/2012 | van der Walt | A61B 34/10 606/102 |
| 10,123,840 | B2 * | 11/2018 | Dorman | A61B 90/06 |
| 10,314,666 | B2 * | 6/2019 | Aghazadeh | A61B 17/60 |
| 2017/0049517 | A1 * | 2/2017 | Felder | A61B 34/30 |
| 2018/0280159 | A1 * | 10/2018 | Hunter | A61B 17/175 |

(Continued)

*Primary Examiner* — Christian A Sevilla

(57) ABSTRACT

Systems, methods and apparatus register a bone for milling during a procedure. A surgeon mills the bone without first performing an explicit registration of a tool relative to the bone. Tool location measurements in combination with a 3-dimensional (3D) model of the patient's bone, such as a segmented CT scan, are used to automatically construct a registration. The 3D model identifies a border where cancellous bone within the bone ends and the cortical bone begins at an inner cortical bone surface. Responsive to movement of the tool within the bone along an initial trajectory, and, using a localizing system to identify the location of tool when in contact with the inner cortical bone surface, a shape/map of the cortical bone is generated and fit to the 3D model automatically to obtain a registration. An updated trajectory may be output such as from 3D implant plan information to guide further milling.

22 Claims, 6 Drawing Sheets

(56) References Cited

U.S. PATENT DOCUMENTS

| | | | |
|---|---|---|---|
| 2018/0296216 A1* | 10/2018 | Shelton, IV | A61B 17/0682 |
| 2019/0000446 A1* | 1/2019 | Shelton, IV | A61B 17/07207 |
| 2019/0008562 A1* | 1/2019 | Melton | A61F 2/30942 |
| 2019/0125468 A1* | 5/2019 | Adams | A61B 34/35 |
| 2019/0380809 A1* | 12/2019 | Fuerst | B25J 13/087 |
| 2020/0000534 A1* | 1/2020 | Grover | A61B 34/35 |
| 2020/0016741 A1* | 1/2020 | He | A61B 34/30 |
| 2020/0383803 A1* | 12/2020 | Wu | A61B 34/10 |

* cited by examiner

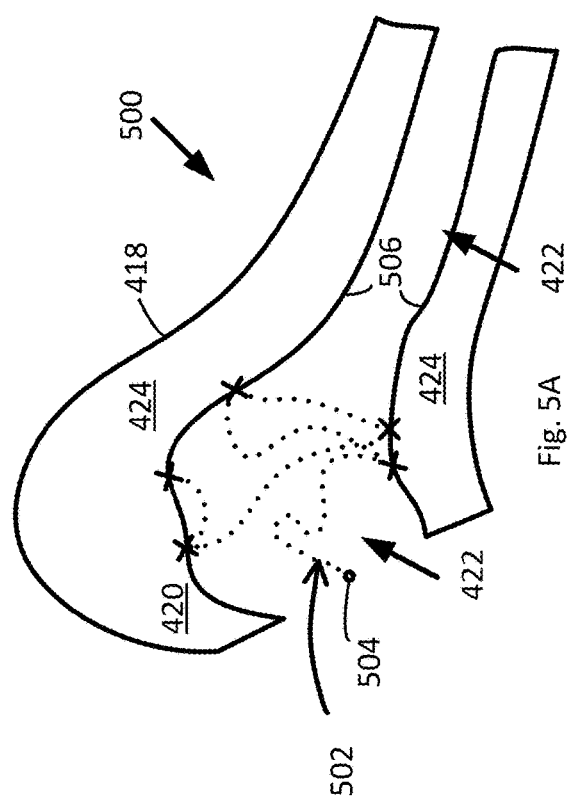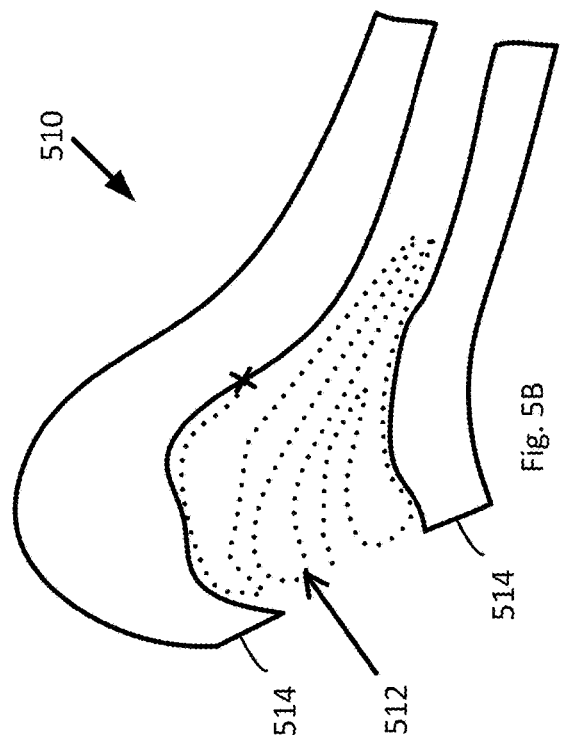

SYSTEM, METHOD AND APPARATUS FOR AUTOMATIC REGISTRATION IN COMPUTER ASSISTED BONE MILLING SURGERY

CROSS REFERENCE

This application claims the benefit under the conditions set forth in 35 U.S.C. 119(e) of U.S. Provisional Application 62/665,730, filed May 2, 2018 and entitled "System, method and apparatus for automatic registration for bone milling surgery", the contents of which are incorporated herein by reference.

FIELD

The present application relates to computer processing to measure objects such as parts of a human body and a surgical tool or implant in a 3D space and more particularly to computer processing for automatic registration in computer assisted bone milling surgery

BACKGROUND

Hip replacements are common orthopedic surgeries wherein at least a portion of a patient's hip joint is replaced with an implant. As shown in FIG. 1 (Source: commons.wikimedia.org/wiki/File:903_Multiaxial_Joint.jpg), the hip joint 100 comprises two main components—the acetabulum 102 and the femoral head 104. A total hip arthroplasty (THA) is a procedure in which a surgeon will replace both the acetabulum 102 and the femoral head 104 with appropriately sized implants. A hemiarthroplasty is a procedure in which the patient's femoral head 104, but not the acetabulum 102, will be replaced with a femoral implant.

As shown in FIG. 2, a femoral implant 200 includes a ball portion 202 and a stem portion 204. The ball portion 202 may be integrally formed with the stem portion 202 or may be removeable to allow the use of different sized ball portions with a given stem. The stem portion 204 of the femoral implant 200 is shaped to fit within the patient's femur. Femoral implants are available in a myriad of shapes to allow a surgeon to select a shape appropriate for any given patient. Femoral implants may even be custom designed to best fit a patient's anatomy. See, e.g., www.tandfonline.com/doi/pdf/10.1080/17453670710014987.

In replacing the femoral head, generally, a surgeon will dislocate the femur from the patient's acetabulum and cut off the femoral head. Once removed, the inner portion of the femur will be exposed. The exposed cross section comprises an outer ring of cortical bone surrounding an inner portion containing cancellous bone. The surgeon will then remove a portion of the cancellous bone to define a cavity inside the femur into which the stem of the femoral implant will be inserted. Removal of the cancellous bone will allow the stem to contact the cortical bone, which is significantly harder than cancellous bone. The femoral stem will be fixed to the cortical bone, such as through use of an adhesive, friction, or other means to keep the stem fixed in position.

Removing the cancellous bone is frequently done using a reamer, a set of broaches, or a milling machine to mill out the bone. It is often desirable to remove only enough cancellous bone to allow the femoral stem to fit within the femur, while preserving any bone which needn't be removed.

SUMMARY

Systems, methods and apparatus register a bone for milling during a procedure. A surgeon mills the bone without first performing an explicit registration of a tool relative to the bone. Tool location measurements in combination with a 3-dimensional (3D) model of the patient's bone, such as a segmented CT scan, are used to automatically construct a registration. The 3D model identifies a border where cancellous bone within the bone ends and the cortical bone begins at an inner cortical bone surface. Responsive to movement of the tool within the bone along an initial trajectory, and, using a localizing system to identify the location of tool when in contact with the inner cortical bone surface, a shape/map of the cortical bone is generated and fit to the 3D model automatically to obtain a registration. An updated trajectory may be output such as from 3D implant plan information to guide further milling.

BRIEF DESCRIPTION OF THE DRAWINGS

FIGS. 5A and 5B are respective illustrations of an initial commanded trajectory and an updated trajectory of a tool for milling a femur.

Figure 2:
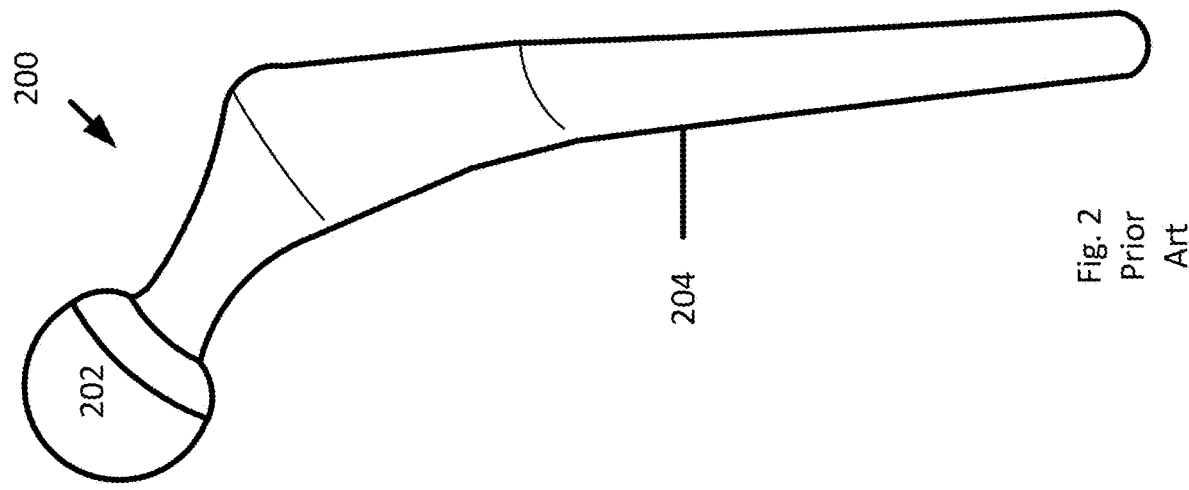
FIG. 2 is a line drawing of a femoral implant in accordance with the prior art.
Figure 1:
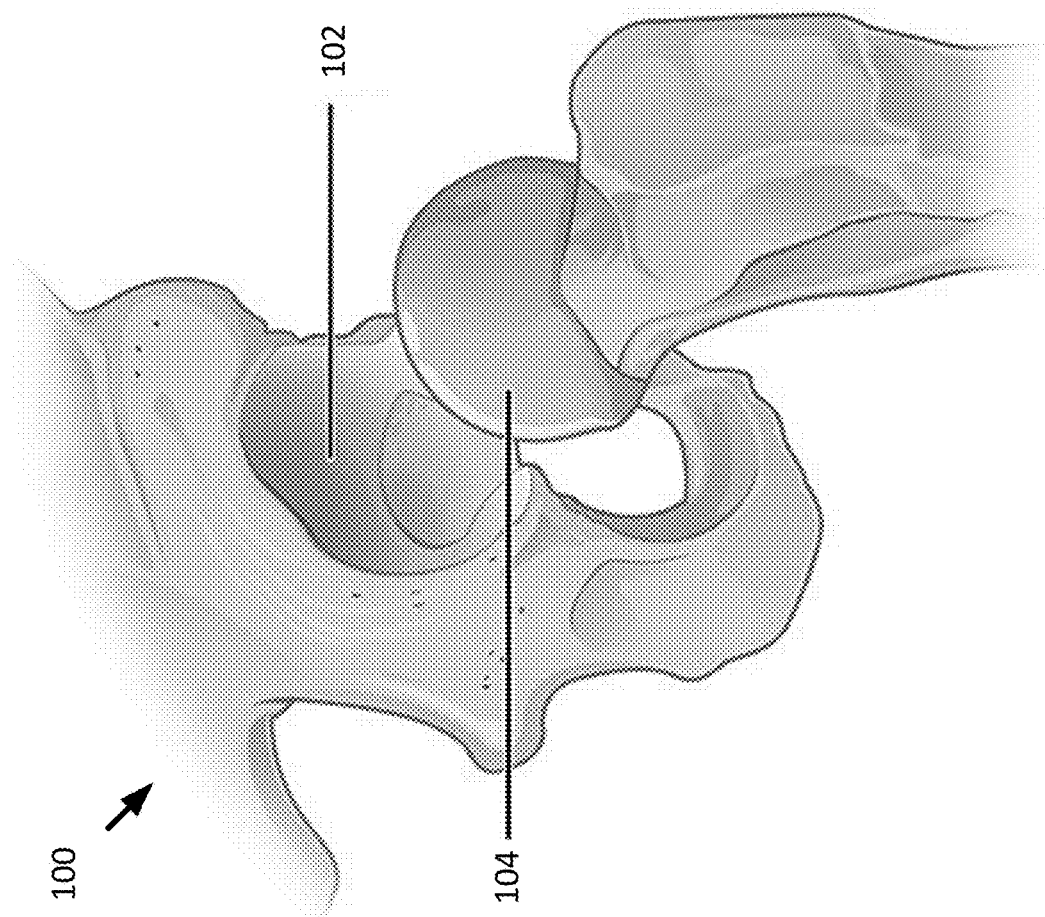
FIG. 1 is an illustration of a hip joint.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light. More than one inventive concept may be shown and described and each may standalone or be combined with one or more others unless stated otherwise.

DETAILED DESCRIPTION

Described are systems, methods and apparatus for registering a bone for milling during a surgical procedure such as a THA. The system described below allows a surgeon to mill the bone without first performing an explicit registration of a tool relative to the bone. The system described below uses measurements of the location of the tool in combination with a 3-dimensional (3D) model of the patient's bone, such as a segmented CT scan. The 3D model may identify the border where cancellous bone within the bone ends and the cortical bone begins. The system may also use a localizing system which may incorporate one or more tracking elements to identify the location of one or more of the surgical tool and an exterior surface of the patient bone. In one example, a camera may be used to detect the position of a first tracking element attached to a surgical tool and a second tracking element attached to a patient bone. In another example, a camera may be attached to a surgical tool and may monitor the position of a tracking element attached to a patient bone.

It will be understood that the camera may be a tracking element for tracking an object such as a part of a patient's anatomy to which the camera is mounted.

The surgeon may insert the milling tool into a predetermined portion of the femur. In one example, the surgeon may insert the milling tool into the center of the exposed internal section of the patient's femur. The milling tool will then be moved within the femur, removing cancellous bone as it moves. The motion of the tool will be tracked continuously as it moves. Accordingly, a "map" may be developed showing the motion of the cutting tool. The milling tool may be moved until it comes into contact with cortical bone. Once the tool contacts cortical bone, the tool may be moved in another direction until it again contacts cortical bone. This may be repeated, and the tool used to identify multiple points of contact with the inner cortical bone. The tool motion may be continuously tracked, and the position recorded at the points of contact. These points may be used to develop a model of the inner cortical surface of the bone. The contact point model may then be compared to the 3D model of the patient's bone. After sufficient contact points of the tool with cortical bone have been identified, the system may be able to fit the physical location of the inner cortical surface of the patient bone with the 3D model of the bone.

The system may then also register the location of the patient bone (for example, using a tracking element, as described below) to the 3D bone model. When the 3D bone model has been registered with the inner cortical surface, as well as with the location of the bone via the tracking element, the system may determine a transformation to correlate the location of the inner cortical surface with the location of the patient bone. The system may then be able to monitor the location of the tool and determine its relative position to the inner cortical surface. When the location of the tool is registered with the location of the patient's anatomy, the system can guide further movement of the tool to allow efficient removal of cancellous bone. In this way, the milling procedure may be performed more quickly, and the amount of cancellous bone to be removed may be minimized. The above registration techniques are shown, and discussed more fully below, with respect to FIGS. 3A and 3B.

The registration of the surgical tool, with the 3D bone model, an inner cortical surface, and a tracker attached to a patient bone will now be described more fully with reference to FIGS. 3A and 3B. As the surgical tool is moved within the inside of the femur, in accordance with an example, the system continuously tracks the position of the surgical tool (e.g. to determine the location of the active end or tip thereof such as the end effector), for example, using a camera and the first tracking element mounted to the tool. (Alternatively, the camera could be on the tool, and the location of the second tracking element coupled to the bone may be determined relative to the camera). At certain points as the tool is moved along an initial trajectory, it contacts cortical bone. When the tool contacts cortical bone, the system saves into a memory the location of the tool and/or the point of contact as a first point. As the tool continues to move along the initial trajectory, the tool contacts additional points, and these locations are also saved by the system. The process (tool movement and contact) continues and additional points saved such that a plurality (n) points are saved. Eventually, a map of the inner cortical surface is developed from these n points. As the map is developed, the system may have the ability to determine the transformation from the map to the 3D bone model.

At each moment of contact, the system knows (i.e. from sensor data received such as from a localizer tracking the tool a processor of the system determines) the location of the tool and/or point of contact. The system also knows the location of the second tracking element (in respect of the bone) at each moment of contact. The system can thus determine a transformation for each point of contact relative to the tool and to the second tracking element, as well as a transformation between the tool and the second tracking element. For example, a camera may track the relative locations of a first tracking element on the tool and a second tracking element on the bone, and develop a transformation therebetween.

Figure 3A:
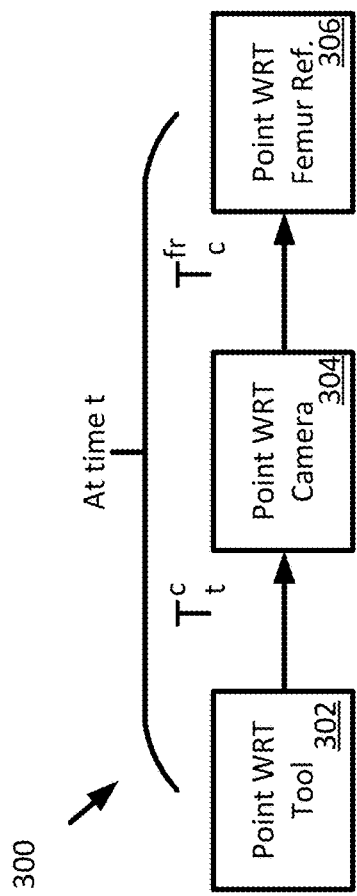
FIGS. 3A and 3B are illustrations of operations comprising transformations and transformation determination between various reference frames.

Thus, FIG. 3A illustrates operations 300 comprising transformations at a time t between various reference frames, for example, for a surgical tool, a camera of a localization system observing the surgical tool in a field of view and a bone, namely a femur, having a 3D bone model and also observed by the camera. In one example, the tool and bone have respective tracker elements mounted thereto for tracking (observing) by the camera. A point with respect to (WRT) the tool 302 at time t may be transformed via a transform $T_t^c$ to a point WRT (the reference frame of) the camera 304. A transform $T_c^{fr}$ may transform the point WRT the camera 304 to a point WRT the femur ref. 306.

As the system collects a myriad of points (e.g. a plurality of n points as described), and develops the appropriate transformations (e.g. $T_t^c$ and $T_c^{fr}$) for each of these points from the tool to the second tracking element, the system can develop a map of the inner cortical surface with respect to the second tracking element.

Figure 3B:
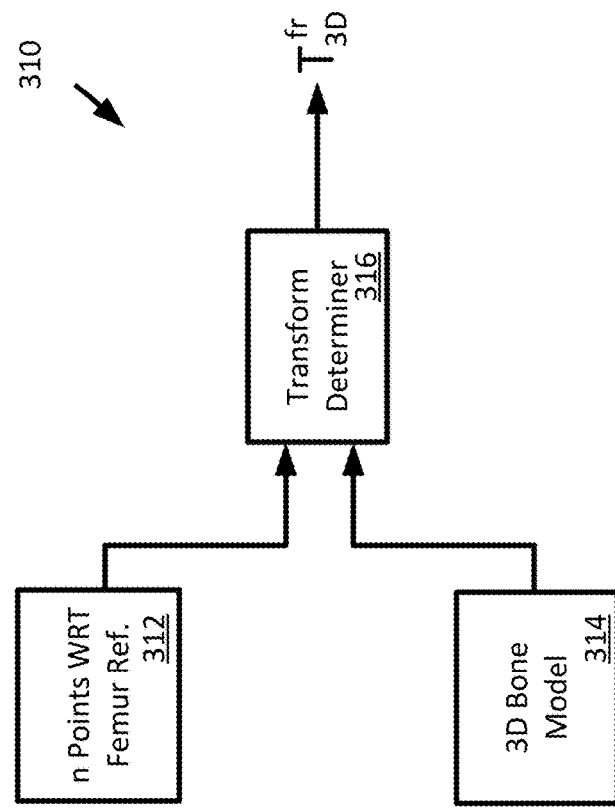

As shown by way of the inputs and operations 310 of FIG. 3B., the system can then use these n points 312 and the 3D bone model to determine a transformation $T_{3D}^{fr}$ (via a transform determiner 316) between the 3D bone model and map of the inner cortical surface to fit the map and the model. For example, the computations may be an optimization (such as an Iterative Closest Point (ICP) operation), where Euclidean distance between points on the 3D bone model and points on the map of the inner cortical surface are minimized, and the coarse registration defines an initial condition for the optimization computations. When the system has determined this transformation $T_{3D}^{fr}$, it then has a transformation between a tool location and the inner cortical surface $T_t^c$ and $T_c^{fr}$, as well as a transformation $T_{3D}^{fr}$ between the inner cortical surface and the 3D bone model. Accordingly, the system can then determine the transformation between the 3D bone model and the tool location (e.g. via inverse operations). The system can then determine or suggest movement of the tool (the updated trajectory) with respect to 3D implant plan information, using the coordinate system of the 3D bone model.

When the transformations have been determined, the location of any of the tool, the inner cortical surface, and the 3D bone model may be expressed in a coordinate system relative to any of the others using the appropriate transformation.

In one exemplary approach, the milling tool may include a sensor. The sensor may be, for example, a multi-dimensional force torque sensor which may indicate the magnitude and direction of a force applied to the end effector of the tool. The sensor may be coupled with a processor which monitors the output of the sensor. The output of the sensor will vary based on the type of bone the tool is in contact with. For example, the force applied to the tool may increase when the tool comes into contact with cortical bone. Additionally, or alternatively, the torque required to maintain a given rotational speed may increase when the tool contacts cortical bone. This sensor may thus be useful in determining when the tool contacts cortical bone and where the contact is made relative to the end effector. The multi-dimensional data may be useful in determine the point of contact relative to the tool position when the contact is made, which may be useful for mapping it to the 3D model of the bone. This may be useful as a tool in a given position may contact a surface in any number of locations around the circumference of an end effector. Moreover, monitoring the multi-dimensional force may allow the system to determine the direction of travel of the tool.

Figure 4:
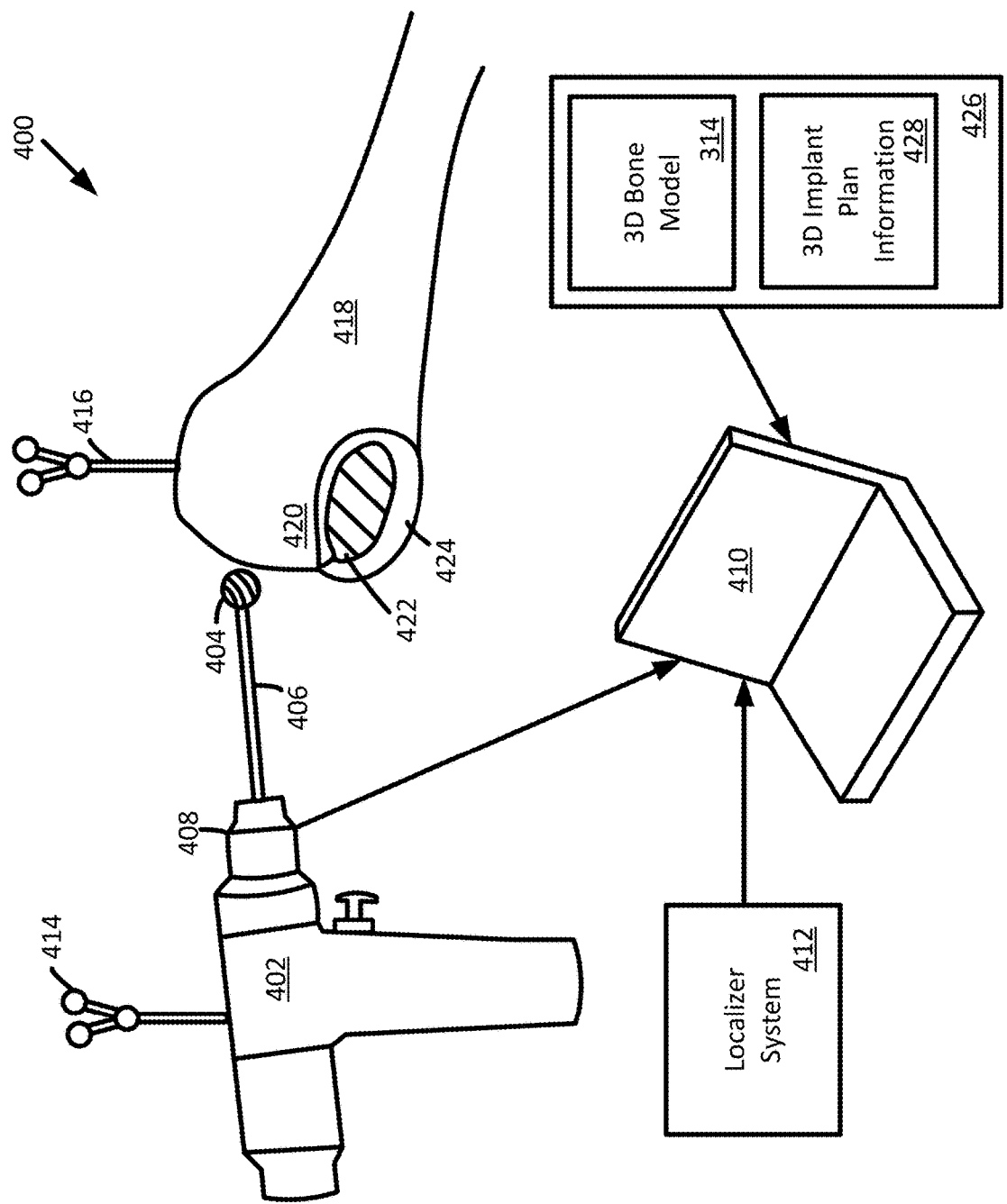
FIG. 4 is an illustration of a system for a bone milling procedure in accordance with one example.

FIG. 4 illustrates components of a system 400 in accordance with an example for automatic registration. System 400, partially described above herein, includes a surgical tool 402 having a milling tip 404 (e.g. an end effector and, here, a high-speed burr) at the end of a shaft 406. The shaft is coupled to a sensor 408. The sensor 408 may be, for example, a multi-dimensional force torque sensor. The sensor 408 is coupled with a computer system (e.g. a computing device 410 such as a laptop, PC or other form factor computing device). Computing device 410 receives sensor information from the sensor 408 of the surgical tool 402. Computing device 410 comprises (or is coupled to) a processor, a storage device, input devices, output devices, communication subsystem, etc. These components of the computing device 410 may be coupled via an internal and/or external communication bus and/or other communication component. Input devices may include a keyboard, a microphone, a button, a pointing device, etc. Output devices may include a display device, a light, a speaker, a haptic device (e.g. vibration device which may be coupled to a surgeon or a tool), etc. In some examples, devices are combined such as I/O devices (e.g. a touchscreen device or similar display with gesture receiving capabilities). The communication subsystem may be configured to communicate wirelessly and/or in a wired manner and in accordance with various protocols and/or standards. Wireless communications may be short range and/or long range. The communication subsystem may be configured to couple computing device 410 (and thus system 400) to a local network and/or to a wide area network, including a global network such as the Internet.

The system 400 includes a localizer system 412 communicatively coupled to the computing device 410 and having a first tracking element 414 coupled to the surgical tool 402 and a second tracking element 416 which is shown coupled to a femur 418. Localizer system 412 also includes a camera (not shown) with a field of view oriented toward the surgical site about femur head 420 to track the first tracking element 414 and the second tracking element 416 during the procedure.

The femur 418, which is not a part of the system 400, is shown with a resected femoral head 420 exposing an inner cancellous bone segment 422 contiguous with a cortical segment 424. The localizer system 412 may determine the relative position of the first tracking element 414 and second tracking element 416. Computing device includes storage device 426 including the 3D model 314 of the patient's bone as well as 3D implant plan information 428. 3D implant plan information 428 may include the shape of the femoral implant, as well as the desired position of the implant within the patient's bone.

Storage device 426 may store instructions thereon configured to cause a processor of computing device 410 to receive the 3D bone model 314, such as a segmented CT scan, associated with the femur 418. The 3D bone model 314 includes the cortical and cancellous segments. The instructions are further configured to cause the processer to receive 3D implant plan information 428.

The milling tool (surgical tool 402) is moved according to an initial commanded trajectory to remove cancellous bone. The initial trajectory, which may be random or guided, will include making contact with the inner surface of cortical bone in a plurality of locations. A guided initial trajectory may be one directed or provided by, for example, a surgical planning or guidance system, which trajectory may be generated by a surgeon, or may be generated by the surgical planning system. A random initial trajectory may simply be one in which a user chooses a trajectory in an ad hoc manner, a trajectory that is not preplanned, or simply one that is not guided. As the milling tool is moved along the initial trajectory, computer device 410 synchronously measures (and stores in the storage device) 3D sensor data comprising the relative position of the first and second tracking elements 414 and 416 and the magnitude and direction of the sensor information from sensor 408. That is the relative positions and the sensor data are associated for example using time so that a relative position at time T is associated with sensor data at time T. The sensor information may include, for example, 3D force torque data indicating the magnitude and direction of the forces and/or torque exerted on the surgical tool (e.g. the end effector at 404) during milling. This 3D sensor information may indicate contact with the inner cortical segment of the femur. Computing device 410 may use the position of the tool at the points of contact to determine a 3D inner cortical shape or map of the femur as described in relation to FIG. 3A.

Computing device 410 may perform a registration of the 3D bone model with the 3D inner cortical shape (map) of the femur as described in relation to FIG. 3B. Computing device 410 may also perform a registration of the 3D bone model with the second tracking element.

After the tool 402 and the femur 418 are registered with the 3D bone model 314, computing device 410 may determine and output an updated trajectory for a desired implant position based on the 3D implant plan information 428 with respect to the 3D bone model 314. The output may guide a surgeon (in the present example) to mill out the required cancellous bone 422 to allow the implant 200 to be positioned into the desired location, while minimizing the removal of additional bone (e.g. cortical or cancellous).

FIG. 5A is an illustration 500 of an exemplary initial commanded trajectory 502 shown in a dotted line of the milling tip 404 of surgical tool 402 (both not shown in FIG. 5A) within a two-dimensional cross section of femur 418. It is understood that while the initial commanded trajectory 502 is shown in two-dimensions for ease of illustration, the initial commanded trajectory may include translation in three dimensions. The initial commanded trajectory 502 may involve growing a milled volume from an initial position 504. The initial position 504 may be, for example, the approximate center of an exposed cancellous portion 422 after the resection of the femoral head 420, and may include an initial orientation of the surgical tool 402 (e.g. the initial orientation of the surgical tool 402 may be an approximate or visual alignment of the tool 402 with respect to the long axis of the bone).

The illustrated initial trajectory 502 includes 5 points of contact, each indicated with an "X" symbol, with the inner cortical surface 506 of the femur 418. The initial commanded trajectory 502 may include avoiding milling cortical bone 424 by detecting, through the one or more sensors 408, contact with cortical bone 424 and adjusting the trajectory 502 accordingly. The initial position 504 may be chosen to provide a coarse registration (of the tool 402 with respect to the bone 418) with at least a minimal degree of accuracy. Similarly, the initial trajectory 502 may be chosen (e.g. by a surgeon) or suggested (e.g. by the system) to provide a trajectory that may minimize the likelihood of unnecessarily removing cancellous or cortical bone, and/or may be chosen to provide an accurate registration with a limited amount of time, movement, and/or bone loss. Analogous registration techniques are described in applicant's U.S. Provisional Patent Application 62/581,307, formalized as U.S. patent application Ser. No. 16/177,948 filed Nov. 1, 2018 each of which are hereby incorporated herein in their respective entireties.

FIG. 5B is an illustration 510 of an exemplary two-dimensional version of an updated trajectory 512. As with the illustrated initial commanded trajectory, it is understood that while the updated trajectory 512 is shown in two-dimensions for ease of illustration, the updated trajectory may include translation in three dimensions. The updated trajectory 512 may be determined and communicated by the computing device 410 to allow the surgeon to remove all required cancellous bone 422 to allow the stem 204 of the femoral implant 200 to be positioned within the femur 418. The updated trajectory 512 may also be optimized. That is, it may be made to be as efficient as possible, thereby speeding up the process of milling all required portions of the cancellous bone 422. Additionally, or alternatively, it may take into account one or more physical characteristics of the surgical tool 402, such as the shape of the tool, the size of the milling end 404, the length of the shaft 406, whether the tool can articulate and at how many points, etc. This optimization may also be used to ensure the tool 402 can remove the relevant bone without colliding with any areas of the patient anatomy (such as the outer cortical layer 514 that is intended to remain intact). Moreover, the updated trajectory 512 may be determined taking into account the initial trajectory 502, recognizing that at least a subset of the cancellous bone 422 will have been removed during the registration.

The surgical tool 402 illustrated in FIG. 4 may be hand operated by a surgeon. An updated trajectory 512 may then be communicated to a user, such as a surgeon. The communication may be made visually, audibly, haptically, or through some combination of the above. For example, the communication may be provided visually on a display screen showing a proposed trajectory, through one or more coloured indicator lights, using graphics, etc. A visual display may overlay a graphic of the current location of the surgical tool with an indication of adjacent or contiguous areas into which the tool should be moved. The communication may be made by, for example, providing haptic feedback or an audible warning, if the user is nearing an area outside the updated trajectory.

Figure 6:
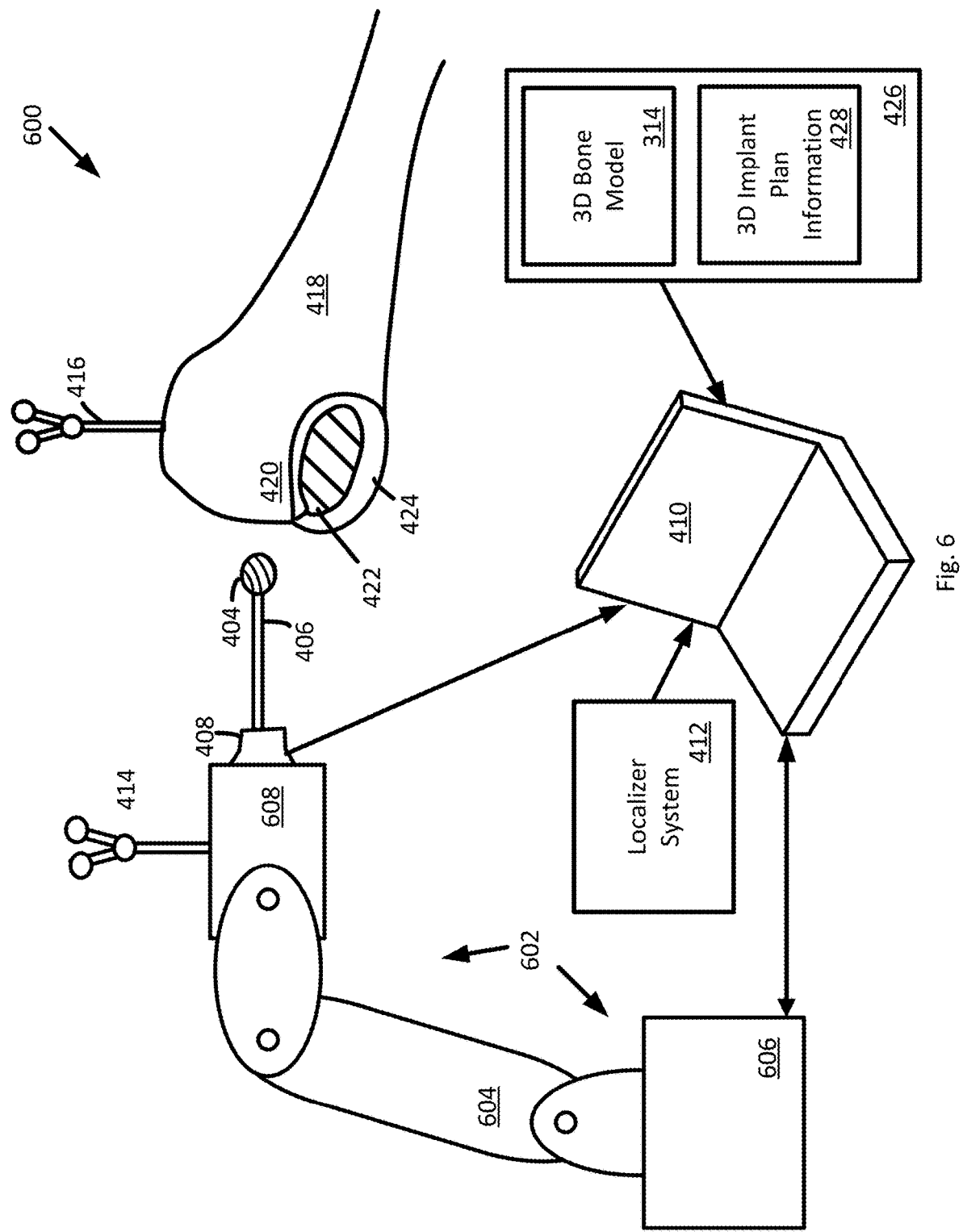
FIG. 6 is an illustration of a system for a robotic bone milling procedure in accordance with another example.

While the system 400 illustrated in FIG. 4 is shown as having a surgical tool 402 that may be handheld, the surgical tool 402 may also be incorporated into a robotic system. FIG. 6 illustrates a system 600 similar to that of FIG. 4, with the surgical tool 402 incorporated into a robotic system 602 and the robotic system coupled for communication with computing device 410.

The robotic system 602 of FIG. 6 includes a robotic arm 604 coupled to a controller 606. The controller 606 may be configured to control a surgical tool 608, similar to handheld surgical tool 402, having a milling tip 404 (e.g. an end effector) and a sensor 408. A surgeon may be able to manually position the milling tool 402 into an initial position by manipulating the robotic system 602. The surgeon may position the tool 608 by physically moving the robotic arm 604 by hand, by manipulating controls (not shown) associated with the robotic arm 604, by inputting coordinates into the controller 606, or otherwise as appropriate. The robotic system 602 may then be manipulated to move the milling tool 608 (e.g. the milling tip 404) along the initial commanded trajectory (e.g. 502). The tool 608 may be moved along the initial trajectory by a surgeon or may be programmed to automatically follow the initial trajectory. After an updated trajectory 512 is output by the computing device 410, the robotic system 602 may be configured to automatically move the surgical tool 608 (e.g. the milling tip 404) along the updated trajectory 512. It is understood that computing device 410 in the present example of system 600 may be configured with any applicable interface hardware and using different instructions to communicate with robotic system 602 as may be necessary.

Note that while the above description is in relation to a replacement of a femoral head in a hip arthroplasty procedure, the same method can be used to provide efficient milling of an appropriate bone for any appropriate procedure. Other exemplary procedures for which the above methods, systems and apparatus may be employed include, but are not limited to, Total Knee Arthroplasty, Total Shoulder Arthroplasty, Total Ankle Arthroplasty, and Total Elbow Arthroplasty.

Moreover, while the above systems 400 and 600 are indicated as reading 3D sensor data using force torque sensors (e.g. 408) to detect the contact of the milling tool (402, 608) with cortical bone 424, the system may also use other methods of making this determination, either alone or in combination. For example, a system could utilize a microphone configured to provide an audio input. The sound of the milling tool interacting with bone will vary based on factors such as the density of the bone. For example, the sound of the milling tool spinning freely will vary from the sound of the milling tool interacting with cancellous bone 422, which will vary meaningfully from the sound of the milling tool interacting with cortical bone 422. The system may be configured to monitor changes in the volume and/or frequency of the sound detected by the microphone and provide an indication to the user. The received audio may thus indicate contact with cancellous bone 422, cortical bone 425, transitions from one bone type to another, etc.

The system could also use one or more sensors (not shown) to detect load on a motor as bone is milled. For example, a sensor may detect changes in rotational torque on a motor shaft, heat created by a spinning motor, voltage or current draw by the motor, or other elements which may vary based on the material through which changes in material may be detected. These sensor readings may be used, either alone or in combination with other received data, to determine contact with bone. It is noted that these alternative sensors may not provide multi-dimensional data and thus, while contact with bone can be detected, the exact location of the contact may be unclear. If however the sensor data is used in combination with, for example, movement data, the system can determine a point of contact with some degree of accuracy.

Exemplary methods and system for registering and/or tracking the location of surgical tools and patient anatomy are described in applicant's U.S. Pat. Nos. 9,713,506 and 9,603,671, the contents of which are hereby incorporated herein by reference in their entirety. It is also understood that a surgical robot may include sensors which may be used in place of or in conjunction with one or more of the elements of the described systems to provide information regarding the location of the surgical tool 608.

The system described herein may eliminate an explicit registration procedure (e.g. localizing multiple points on the surface of the bone and matching to a segmented CT), and instead allow for an implicit registration based on a tracked surgical tool (e.g. a high-speed burr tool). As registration is time consuming, the system described herein can save time by performing registration and initial milling in parallel. Moreover, while traditional registration may require a lot of human effort or skill, aspects of this disclosure could be automated and performed by a robotic system.

In summary, in an exemplary (robotic) embodiment, the operating principle is initially as follows. The milling tool of the system moves around and every time it contacts the inner cortical surface of a bone, the system "remembers" that location. After learning a sufficient number of contact points with cortical bone, the system performs a mapping between the contact points and a segmented 3D model of the inner surface of a cortical bone. Once the map has been determined, the system "knows" exactly where the milling tool is relative to the bone, and it can proceed to follow a trajectory in accordance with a surgical plan.

It is noted that, a robot is not a required element of the system. As mentioned above, the surgical tool can be a handheld tool operated by a surgeon. A handheld tool may be entirely mobile, or may be affixed to a mechanical arm (which may or may not be powered). Additionally, a surgeon may perform a subset of the steps described for the system, and a robot may perform other steps. For example, a surgeon may execute the initial trajectory before the tool is registered and, once the updated (post registration) trajectory is calculated, the information may be fed back to the surgeon to execute the updated trajectory In another example, the surgeon may execute the initial trajectory, and the robot automatically executes updated trajectory. In still another example, the surgeon may set the initial position for a robot, and the robot executes initial trajectory and updated trajectory.

It is noted that while the system and method above are described as measuring a first density associated with cancellous bone and a second density associated with cortical bone, it is to be understood that the density of bone of any type may vary. The varying density may be determined via the output of a sensor that is continuously monitored as the surgical tool is moved and the associated bone density may be used for registration and/or mapping, for example, by comparing the changing density with data associated with density included in a 3D bone model.

While the system and method above are described as occurring after the resection of a patient's femoral head, it is understood that the system may be used and method steps may occur prior to, or in conjunction with the resection of the femoral head. For example, a force torque sensor may be used to determine when a surgical tool makes first contact with an exterior surface of a patient bone, which may be a sacrificial cortical surface. The surface may be chosen based on a surgical plan indicating that the surface will be removed as part of the procedure. The points of contact may be monitored, in a manner as described above, and used to register the location of the bone with the 3D model.

While the surgical tool above is described as having a milling tool used for the registration, it is understood that other tools may be used. For example, a ruby tip may be used to probe various points within a surgical area. Additionally, a milling tool may be used, but the rotating end effector need not be spinning. This may be useful as it could prevent additional bone from being removed during the initial registration process, and may allow external cortical bone to be used for registration.

Thus there is illustrated and described a system to determine the location of an inner cortical surface of a bone during a surgical procedure. The system may comprise a surgical tool; a localization system comprising a first tracking element coupled to the surgical tool and a second tracking element coupled to a bone, the bone having a cortical segment having an outer surface and an inner surface, the inner surface defining a cancellous segment contiguous with the inner surface, the localization system providing localization data associated with a location of the first tracking element and a location of the second tracking element to determine a relative position; one or more sensors coupled with the surgical tool and configured to output sensor data; and, a non-transient storage element storing computer instructions.

The instructions may be executed by a processor, such as by a processor of a computing device, to configure the processor (and hence the computing device) to: receive a 3D bone model comprising the cortical segment and the cancellous segment; receive 3D implant plan information with respect to the 3D bone model; receive the localization data and the sensor data in response to the surgical tool travelling along an initial commanded trajectory, the initial commanded trajectory including a plurality of contacts of an end effector of the surgical tool with the inner cortical surface and the sensor data indicating contact with the inner cortical surface; synchronously measure relative positions of the first tracking element and the second tracking element using the localization data and associating the relative positions with the sensor data; determine 3D inner cortical shape information based at least in part on the sensor data and the relative positions; register the 3D bone model with the 3D inner cortical shape information; register the 3D bone model to the second tracking element; and command an updated trajectory for a desired implant position based on the 3D implant plan information with respect to the 3D bone model.

The surgical tool may comprise a milling tool and the end effector may comprise a milling tip. The milling tip may mill cancellous bone while traversing the initial commanded trajectory.

The one or more sensors may comprise a multi-dimensional force torque sensor to output sensor data comprising a magnitude and a direction of one or more of forces and torques on the milling tool. The sensor data of the multi-dimensional force torque sensor may indicate at least one of the force or torque applied to the milling tool. The sensor data of the multi-dimensional force torque sensor may indicate a transition from contact with a material of a first density to a material of a second density. The material of a first density may comprise cancellous bone and the material of a second density may comprise cortical bone.

The initial commanded trajectory may be responsive to a user physically manipulating the milling tool. The initial commanded trajectory may define a milled volume from an initial position. The initial commanded trajectory may be defined to avoid damage to cortical bone by detecting contact with cortical bone based on the sensor data and adjusting the trajectory accordingly.

The surgical tool may be coupled to a robotic system. The initial commanded trajectory may begin at an initial position based on a user manual positioning of the surgical tool, and the instructions may configure the processor to command the surgical tool, via the robotic system, to continue automatically following a trajectory. The bone may comprise a femur, and the initial position may comprise the approximate center of an exposed cancellous portion. The initial position may be chosen after the resection of a femoral head. The initial position may comprise an approximate orientation of the surgical tool with respect to the femoral canal.

The one or more sensors may comprise a microphone and the sensor data may comprise a signal indicative of the sound made by the milling machine as it mills one or more types of bone.

The registration of the 3D bone model with the 3D inner cortical shape information may comprise an optimization, where Euclidean distance between points on the 3D bone model and points on a map of the inner cortical surface are minimized. The optimization may include an Iterative Closest Point (ICP) operation. A coarse registration may define an initial condition for optimization computations. An initial position may be chosen to provide the coarse registration of the surgical tool with respect to the bone with at least a minimal degree of accuracy.

It is understood that the system may comprise a processor of a computing device and may comprise the computing device, among other components.

Figure 7:
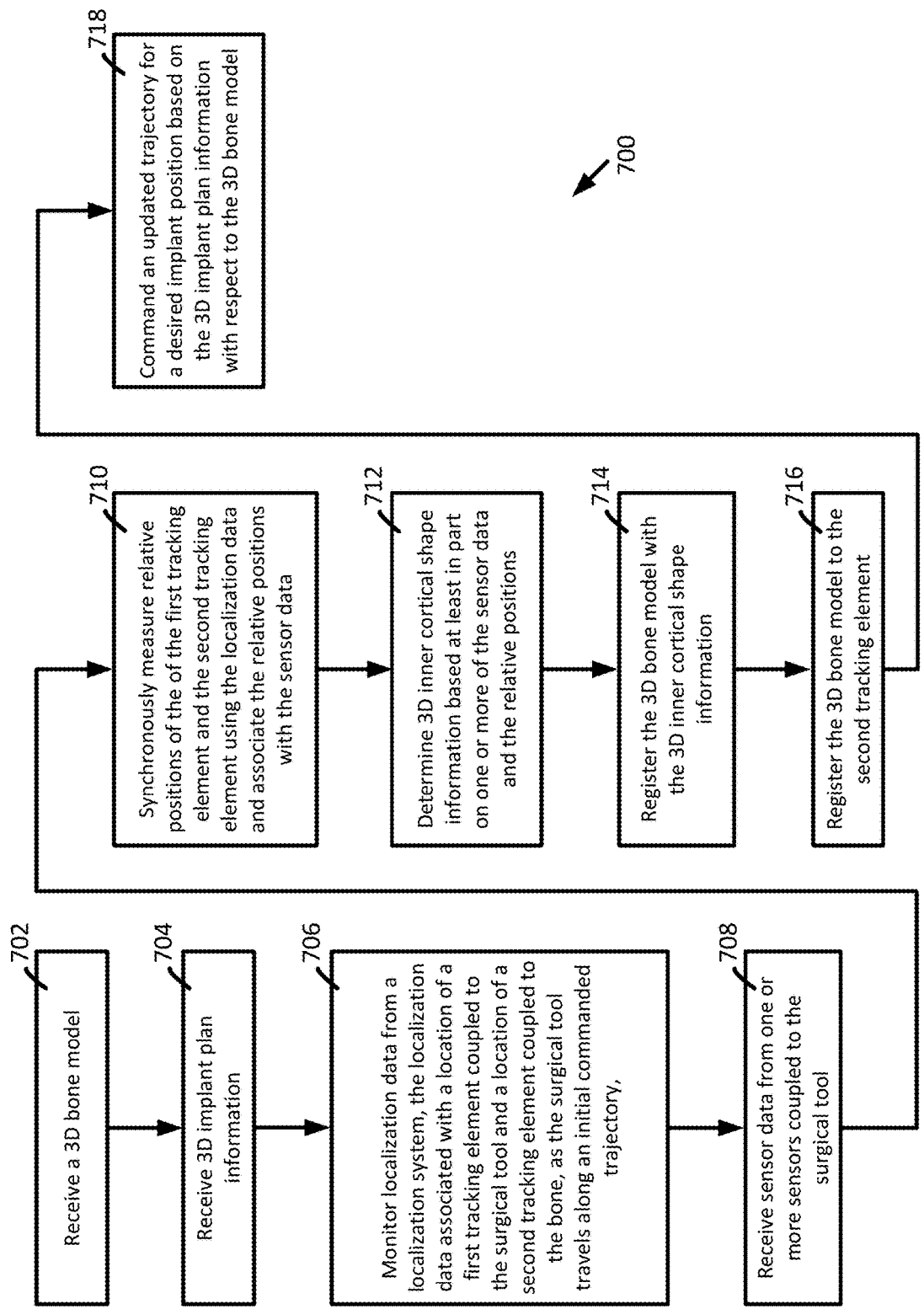
FIG. 7 is a flowchart of operations in accordance with an example herein.

FIG. 7 illustrates operations 700 to provide a method of using a surgical tool. The method may be performed by a computing device such as described. At 702 operations receive a 3D bone model identifying a cortical segment and a cancellous segment of a bone of a patient, the cortical segment contiguous with the cancellous segment. At 704 operations receive 3D implant plan information with respect to the 3D bone model. At 706 operations monitor localization data from a localization system as the surgical tool travels along an initial commanded trajectory, the initial commanded trajectory including a plurality of contacts of an end effector of the surgical tool with the inner cortical surface. The localization data is associated with a location of a first tracking element coupled to the surgical tool and a location of a second tracking element coupled to the bone. At 708 operations receive sensor data from one or more sensors coupled to the surgical tool. The sensor data is received in response to the surgical tool travelling along the initial commanded trajectory and the sensor data indicates contact with the inner cortical surface. At 710 operations synchronously measuring relative positions of the first tracking element and the second tracking element using the localization data and associating the relative positions with the sensor data.

At 712 operations determine 3D inner cortical shape information based at least in part on one or more of the sensor data and the relative positions. At 714 operations register the 3D bone model with the 3D inner cortical shape information. At 716 operations register the 3D bone model to the second tracking element. And at 718 operations command an updated trajectory for a desired implant position based on the 3D implant plan information with respect to the 3D bone model.

There is provided a tangible non-transitory computer readable medium storing instructions which when executed by a computing device configure the computing device to perform any of the methods as described.

While the systems and methods described above are discussed in the context of identifying the transition from cancellous bone to cortical bone, it is also understood that the systems and methods described herein may be used to detect a transition from a material of higher density (such as cortical bone) to a material of lower density (such as cancellous bone) or to a state of non-contact. For example, in a cranial operation, such a system may be used to determine when a surgical tool has cut through bone and provide warning to a user to avoid sensitive tissue, such as brain tissue.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise. By way of example and without limitation, references to a computing device comprising a processor and/or a storage device includes a computing device having multiple processors and/or multiple storage devices. Herein, "A and/or B" means A or B or both A and B.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A system to determine the location of an inner cortical surface of a bone during a surgical procedure comprising:
   a surgical tool;
   a localization system comprising a first tracking element coupled to the surgical tool and a second tracking element adapted to be coupled to a bone, the bone having a cortical segment having an outer surface and an inner surface, the inner surface defining a cancellous segment contiguous with the inner surface, the localization system providing localization data associated with a location of the first tracking element and a location of the second tracking element to determine a relative position;
   one or more sensors coupled with the surgical tool and configured to output sensor data; and,
   a non-transient storage element storing computer instructions, which instructions when executed by a processor configure the processor to:

receive a 3D bone model comprising the cortical segment and the cancellous segment;
receive 3D implant plan information with respect to the 3D bone model;
receive the localization data and the sensor data in response to the surgical tool travelling along an initial commanded trajectory, the initial commanded trajectory including a plurality of contacts of an end effector of the surgical tool with the inner cortical surface and the sensor data indicating contact with the inner cortical surface;
synchronously measure relative positions of the first tracking element and the second tracking element using the localization data and associating the relative positions with the sensor data;
determine 3D inner cortical shape information based at least in part on the sensor data and the relative positions;
register the 3D bone model with the 3D inner cortical shape information;
register the 3D bone model to the second tracking element; and
command an updated trajectory for a desired implant position based on the 3D implant plan information with respect to the 3D bone model.

2. The system of claim 1 wherein the surgical tool comprises a milling tool and the end effector comprises a milling tip.

3. The system of claim 2 wherein the milling tip mills cancellous bone while traversing the initial commanded trajectory.

4. The system of claim 1 wherein the one or more sensors comprises a multi-dimensional force torque sensor to output sensor data comprising a magnitude and a direction of one or more of forces and torques on the milling tool.

5. The system of claim 4 wherein the sensor data of the multi-dimensional force torque sensor indicates at least one of the force or torque applied to the milling tool.

6. The system of claim 5 wherein the sensor data of the multi-dimensional force torque sensor indicates a transition from contact with a material of a first density to a material of a second density.

7. The system of claim 6 wherein the material of a first density comprises cancellous bone and the material of a second density comprises cortical bone.

8. The system of claim 1 wherein the initial commanded trajectory is responsive to a user physically manipulating the milling tool.

9. The system of claim 1 wherein the initial commanded trajectory defines a milled volume from an initial position.

10. The system of claim 1 wherein the initial commanded trajectory is defined to avoid damage to cortical bone by detecting contact with cortical bone based on the sensor data and adjusting the trajectory accordingly.

11. The system of claim 1 wherein the surgical tool is coupled to a robotic system.

12. The system of claim 11 wherein the initial commanded trajectory begins at an initial position based on a user manual positioning of the surgical tool, and the instructions configure the processor to command the surgical tool, via the robotic system, to continue automatically following a trajectory.

13. The system of claim 12 wherein the bone comprises a femur, and the initial position comprises an approximate center of an exposed cancellous portion.

14. The system of claim 13 wherein the initial position is chosen after the resection of a femoral head.

15. The system of claim 12 wherein the initial position comprises an approximate orientation of the surgical tool with respect to the femoral canal.

16. The system of claim 1 wherein the one or more sensors comprises a microphone and the sensor data comprises a signal indicative of the sound made by the milling machine as it mills one or more types of bone.

17. The system of claim 1 wherein the registration of the 3D bone model with the 3D inner cortical shape information comprises an optimization, where Euclidean distance between points on the 3D bone model and points on a map of the inner cortical surface are minimized.

18. The system of claim 17 wherein the optimization comprises an Iterative Closest Point (ICP) operation.

19. The system of claim 17 wherein a coarse registration defines an initial condition for optimization computations.

20. The system of claim 19 wherein an initial position is chosen to provide the coarse registration of the surgical tool with respect to the bone with at least a minimal degree of accuracy.

21. A method of using a surgical tool comprising:
receiving a 3D bone model identifying a cortical segment and a cancellous segment of a bone of a patient, the cortical segment contiguous with the cancellous segment;
receiving 3D implant plan information with respect to the 3D bone model;
monitoring localization data from a localization system, the localization data associated with a location of a first tracking element coupled to the surgical tool and a location of a second tracking element coupled to the bone, as the surgical tool travels along an initial commanded trajectory, the initial commanded trajectory including a plurality of contacts of an end effector of the surgical tool with an inner cortical surface of the bone;
receiving sensor data from one or more sensors coupled to the surgical tool, the sensor data received in response to the surgical tool travelling along the initial commanded trajectory and the sensor data indicating contact with the inner cortical surface;
synchronously measuring relative positions of the first tracking element and the second tracking element using the localization data and associating the relative positions with the sensor data;
determining 3D inner cortical shape information based at least in part on one or more of the sensor data and the relative positions;
registering the 3D bone model with the 3D inner cortical shape information;
registering the 3D bone model to the second tracking element; and
commanding an updated trajectory for a desired implant position based on the 3D implant plan information with respect to the 3D bone model.

22. A tangible non-transitory computer readable medium storing instructions which when executed by a computing device configure the computing device to perform a method in accordance with claim 21.

* * * * *